(12) United States Patent
Gao et al.

(10) Patent No.: US 8,762,084 B2
(45) Date of Patent: Jun. 24, 2014

(54) MULTIPLE EXCITATION CAPACITANCE POLLING FOR ENHANCED ELECTRONIC CAPACITANCE TOMOGRAPHY

(75) Inventors: Robert X. Gao, Manchester, CT (US); Zhaoyan Fan, Willimantic, CT (US)

(73) Assignee: The University of Connecticut, Farmington, CT (US)

( * ) Notice: Subject to any disclaimer, the term of this patent is extended or adjusted under 35 U.S.C. 154(b) by 610 days.

(21) Appl. No.: 12/826,314

(22) Filed: Jun. 29, 2010

(65) Prior Publication Data

US 2010/0332170 A1 Dec. 30, 2010

Related U.S. Application Data

(60) Provisional application No. 61/221,806, filed on Jun. 30, 2009.

(51) Int. Cl.
*G01R 25/00* (2006.01)

(52) U.S. Cl.
USPC ............................................................ 702/65

(58) Field of Classification Search
None
See application file for complete search history.

(56) References Cited

U.S. PATENT DOCUMENTS

| 8,264,246 | B2 * | 9/2012 | Mahalingam et al. | 324/693 |
| 2007/0133746 | A1 * | 6/2007 | Ortiz Aleman et al. | 378/59 |
| 2010/0303321 | A1 * | 12/2010 | McEwan et al. | 382/131 |

FOREIGN PATENT DOCUMENTS

| GB | 2454925 A | 5/2009 |
| ZA | 2003/3451 | 11/2003 |

OTHER PUBLICATIONS

Notification Concerning Transmittal of International Preliminary Report on Patentability for Int'l Application No. PCT/US2010/040446; Date Mailed: Jan. 12, 2012.

International Search Report and the Written Opinion for PCT/US2010/040446, mailing date Sep. 29, 2010.

Gamio, J. C., "A Comparative Analysis of Single- and Multiple-Electrode Excitation Methods in Electrical Capacitance Tomography," *Meas. Sci. and Technol.*, 13: 1779-1809 (2002).

McEwan, A., et al., "Electrode Circuits for Frequency- and Code-Division Multiplexed Impedance Tomography," *Biomedical Circuits and Systems Conference, 2007 IEEE*, Piscataway, NJ: 130-133 (2007).

McEwan, A., et al., "Wide-Bandwitdth, High Frame Rate Electrical Impedance Tomography/Spectrscopy. A Code Division Multiplexing (CDM) Approach," *Biodevices 2008—Proceedings of the 1st International Conference on Biomedical Electronics and Devices*, Funchal, Madeira, Portugal, 2: 196-203 (2008).

(Continued)

*Primary Examiner* — Aditya Bhat
(74) *Attorney, Agent, or Firm* — Hamilton, Brook, Smith & Reynolds, P.C.

(57) ABSTRACT

Disclosed herein is a novel sensing technique, termed Multiple Excitation Capacitance Polling (MECaP), that improves the efficiency of Electrical Capacitance Tomography (ECT). Unlike traditional alternating current techniques, where excitation signal is applied to an electrode one at a time, MECaP involves simultaneously applying multiple excitation signals, in a progressively increasing fashion, to multiple electrodes on an ECT sensor. The received signals are filtered or otherwise decomposed (e.g., Fourier transformed) into different components, and the individual components are used to generate an image of the article or substance disposed between the electrodes. Because multiple capacitances can be simultaneously measured as a consequence, scanning with MECaP can significantly increase the image scanning speed. For example, scanning with MECaP may enable frames rates of tens of kHz for imaging dynamic processes such as engine combustion.

29 Claims, 8 Drawing Sheets

(56) References Cited

OTHER PUBLICATIONS

Hasekioğlu, O. and K, Kiymik, "Multiple Simultaneous Excitation Electrical Impedance Tomography Using Low Crosscorrelated Signals," *Proceedings of the International Society for Optical Engineering (SPIE)*, USA, 1818(3): 1256-1263 (1992).

Yang, W. Q., "Further Developments in an AC-Based Capacitance Tomography System," *Review of Scientific Instruments*, 72(10): 3902-3907 (2001).

He, R., et al., "Engine Flame Imaging Using Electrical Capacitance Tomography," *Electronics Letters*, 30(7): 559-560 (1994).

Reinecke, N. and Mewes, D., "Recent Developments and Industrial/Research Applications of Capacitance Tomography," *Meas. Sci. Technol.*, 7: 233-246 (1996).

Alme, K. J., and Mylvaganam, S., "Comparison of Different Measurement Protocols in Electrical Capacitance Tomography Using Simulations," *IEEE Transactions on Instrumentation and Measurement*, 56(6): 2119-2130 (2007).

Olmos, A. M., et al., "Development of an Electrical Capacitance Tomography System Using Four Rotating Electrodes," *Sensors and Actuators A*, 148: 366-375 (2008).

Yang, W. Q., et al., "Analysis of the Effect of Stray Capacitance on an AC-Based Capacitance Tomography Transducer," *IEEE Transactions on Instrumentation and Measurement*, 52(5): 1674-1681 (2003).

Gonzalez-Nakazawa, A., et al., "Transient Processes and Noise in a Tomography System: An Analytical Case Study," *IEEE Sensors Journal*, 5(2): 321-329 (2005).

Waterfall, R. C., et al., "Flame Visualizations Using Electrical Capacitance Tomography (ECT)," *Proceedings of SPIE Conference*, Boston, MA, 4188: 242-250 (2001).

Huang, S. M., et al., "Capacitance-Based Tomographic Flow Imaging System," *Electronics Letters*, 24(7): 418-419 (1988).

Waterfall, R. C., et al., "Combustion Imaging from Electrical Impedance Measurements," *Meas. Sci. Technol.*, 7: 369-374 (1996).

Yang, W. Q., "Hardware Design of Electrical Capacitance Tomography Systems," *Meas. Sci. Technol.*, 7: 225-232 (1996).

Isaksen, Ø., "A Review of Reconstruction Techniques for Capacitance Tomography," *Meas. Sci. Technol.*, 7: 325-337(1996).

Alme, K. J. and Mylvaganam, S., "Electrical Capacitance Tomography—Sensor Models, Design, Simulations, and Experimental Verification," *IEEE Sensors Journal*, 6(5): 1256-1266 (2006).

Williams, R. A. and Beck, M. S., "Capacitance Sensors—A Major Case Study" In *Process Tomography: Principles, Techniques and Applications*, (Oxford, U.K.: Butterworth-Heinemann), pp. 83-107 (1995).

Williams, R. A. and Beck, M. S., "Electrical Impedance Tomography for Flow Imaging of Conducting Fluids—An Outline" In *Process Tomography: Principles. Techniques and Applications*, (Oxford, U.K.: Butterworth-Heinemann), pp. 105-110 (1995).

Wolański, P, et al., "Flame Visualizations in a Cylindrical Chamber by Means of Electrical Capacitance Tomography (ECT)," *Archivum Combustionis*, 20(3-4): 9-17 (2000).

McEwan, A., et al., "Design and Calibration of a Compact Multifrequency EIT System for Acute Stroke Imaging," *Physiological Measurement*, 27(5): 199-210.

Nguyen, D.T., et al., "A Review on Electrical Impedance Tomography for Pulmonary Perfusion Imaging," *Physiological Measurement*, 33(6): 695-706 (2012).

Jongschaap, H., et al., "Electrical Impedance Tomography: A Review of Current Literature," *European Journal of Radiology*, 18: 165-174 (1994).

* cited by examiner

MULTIPLE EXCITATION CAPACITANCE POLLING FOR ENHANCED ELECTRONIC CAPACITANCE TOMOGRAPHY

RELATED APPLICATION

This application claims the benefit of U.S. Provisional Application No. 61/221,806, filed on Jun. 30, 2009, the entire teachings of which are incorporated herein by reference.

BACKGROUND

Electrical capacitance tomography (ECT) is a technique to determine the dielectric permittivity distribution in the interior of an object from external capacitance measurements. ECT's advantages over conventional tomographic techniques include non-intrusiveness, non-destruction, no radiation hazard, and low cost. In industry, ECT has found many applications, such as measurement of gas/liquid and gas/solid flows in pipelines; analysis of dynamic processes in fluidized beds; monitoring of mixing and separation processes; visualization of combustion flames in engine cylinders; and detection of leakage from buried water pipes.

ECT enables insight into the material distribution within a closed vessel, and consequently, into the governing mechanism in processes occurring within the vessel, without disturbing the processes themselves. Research on ECT encompasses sensor design, capacitance measuring circuit design, and image reconstruction. While sensor and circuit design involve hardware, image reconstruction typically involves software.

FIG. 1 shows a typical ECT system 100 that includes the following components: (1) an ECT sensor 110 that registers physical responses from the object being measured; (2) excitation and measurement circuitry 120 that drives the sensor 110 and conditions the received signals; and (3) a computer-based data acquisition and channel switching system 130 to provide control signals 134 for the sequential excitation of the electrodes. The computer-based system 130 can also reconstruct tomographic images of the object based on the measured data 132.

As shown in FIG. 1, the ECT sensor 110 consists of a total of M electrodes 111a-111m that are mounted symmetrically outside of a cylindrical container 114. Traditionally, during each scanning frame, an excitation signal in the form of an alternating current (AC) voltage is applied to one of the electrodes, e.g., electrode 111a, and the remaining electrodes 111b-111m are kept at ground potential to act as detector electrodes. Subsequently, the voltage potential at each of the remaining electrodes 111b-111m is measured, one at a time, by the measurement electronics 120 to determine the inter-electrode capacitance. Specifically, in the first round of the measurements, inter-electrode capacitance is measured between electrodes 111a and 111b. Next, capacitance is measured between electrodes 111a and 111c, then between electrode 111a and 111d, and so on. In the second round of measurements, the capacitances is measured first between electrodes 111b and 111c, then between electrodes 111b and 111d, and so on. Measurement cycles continue with each individual electrode assuming the role of an excitation source and a detector, alternately, until all the inter-electrode capacitances are measured.

The measured capacitances can be then represented in a matrix and used to reconstruct the tomographic image of the object within the cylindrical container. Analytically, with M electrodes 111a-111m in the ECT sensor 110, a total number of H independent capacitance measurements take place, where $H=M(M-1)/2$. In ECT systems reported in the literature, the number of electrodes M was typically chosen to be 6, 8, 12, 16, and 32. Thus, the number of independent capacitance measurements H was 15, 28, 66, 120, and 496, respectively.

The number of capacitance measurements to be performed by the ECT sensor is a parameter that affects the quality of the reconstructed image. Increasing the number of electrodes improves the resolution of the reconstructed image. For a given measurement area, however, increasing the number of electrodes also causes each electrode to have a smaller surface, thus decreasing the magnitude of the inter-electrode capacitance, which, in turn, leads to a lower signal-to-noise ratio (SNR) given fixed background noise.

One solution to this problem is the grouping technique, which involves combining two or more electrodes into one segment to increase the magnitude of the received signal, as shown in FIG. 2. However, excitation of the electrodes within each segment is still performed in steps of one electrode at a time only. This grouping configuration is repeated along the sensor circumference by shifting the connection by one electrode in each measurement to form a series of independent measurements.

FIG. 2 shows an eight-electrode sensor 110 operated in the four-segment mode. The total surface area covered by electrodes 111a-111m equals that of a four-electrode ECT sensor without segmentation, so the SNR remains the same as that of the four-segment sensor. After measuring the first six capacitance values for a first configuration 202, the electrodes 111a-111m are re-connected in a second configuration 204. This can be viewed as a rotation of the four electrodes by θ=45°. As a result, the total number of independent measurements performed by the ECT electronics in each scanning frame is twice as high (twelve vs. six) compared to a conventional four-electrode sensor, thus achieving higher resolution for better image reconstruction.

Scanning speed is an important parameter of an ECT system, as it determines the usability of ECT for on-line, real-time applications involving fast changing dynamics, such as combustion or explosion within an enclosure. Currently, the maximum scanning speed achieved by ECT is about 300-1,000 frames/second. While satisfactory for general applications, this speed is far lower than what can be achieved with optical methods, although optical methods need direct access to the process to be monitored and thus are subject to various constraints (e.g., blockage of the line of sight) in real-world environments. For engine combustion process imaging, which is not easily monitored using optical methods, it is desirable to resolve the process at every crank angle (i.e., in 1° increments) at crank rotational speeds of up to 6,000 rev/min. This requires an ECT system that can collect data at a speed of up to 36,000 frames/second.

SUMMARY

Embodiments include an apparatus, corresponding method, and corresponding non-transitory computer-readable medium with code for electronic capacitance tomography that includes measuring multiple excitation signals simultaneously. Source and receiver electrodes capacitively coupled together measure a spatial distribution of a substance within capacitive distance of at least one pair of the source and receiver electrodes. An excitation module coupled to the source electrodes excites simultaneously each source electrode with a different excitation signal. A measurement module coupled to the receiver electrodes simultaneously measures capacitance between pairs of source and receiver electrodes. The measured capacitances represent the spatial distribution of the substance.

In some embodiments, the different excitation signals are at different frequencies. Alternatively, the different excitation signals may be modulated with different codes. In any case, each receiver electrode may receive simultaneously excitation signals from more than one source electrode. The measurement module may be configured to measure capacitances between each receiver electrode and every source electrode simultaneously.

Further embodiments may include a discrimination module coupled to the measurement module. The discrimination module may be configured to discriminate among signals received simultaneously at a given receiver electrode from more than one source electrode, possibly with a filter bank configured to filter excitation signals at different frequencies. Alternatively, the discrimination module may decompose (e.g., Fourier transform) the signals detected by the receiver electrodes to measure the capacitances.

Still other embodiments may include an imaging module coupled to the measurement module. The imaging module may be configured to convert the measured capacitances to an indication, such as a 3D rendering, of the spatial distribution of the substance. Alternatively, a storage module coupled to the measurement module may store the measured capacitances, which can be converted into indications of the spatial distribution of the substance with a postprocessing module.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments of the invention follows.

Traditional alternating current (AC) electronic capacitance tomography (ECT) involves applying an excitation signal at each time instance to one of the M electrodes of an ECT sensor and measuring the voltage at the other electrodes to determine the inter-electrode capacitance. Such a timely sequential, single-electrode excitation method is time consuming, especially when M is relatively large. As an alternative, embodiments of the present inventive methods apply multiple excitation signals to multiple electrodes at each time instance, thus enabling simultaneous measurement of more than one inter-electrode capacitance, thereby improving the efficiency of AC-based ECT measurement systems. The present inventive method, which is known as Multiple Excitation Capacitance Polling (MECaP), involves:

(1) simultaneously applying N AC excitation signals, each of which is at a different frequency, e.g., $f_1, f_2, \ldots f_N$, to N respective electrodes in an ECT sensor with M electrodes (N≤M−1);

(2) detecting the signals from each of the N excited electrodes with one of the remaining electrodes (M−N);

(3) filtering the received signals with a bank of N bandpass filters whose central frequencies are tuned to $f_1, f_2, \ldots f_N$, respectively; and (4) calculating the individual inter-electrode capacitance from either the ratio of the excitation signal magnitude to that of the received signal or phase changes in the received signal.

Figure 1:
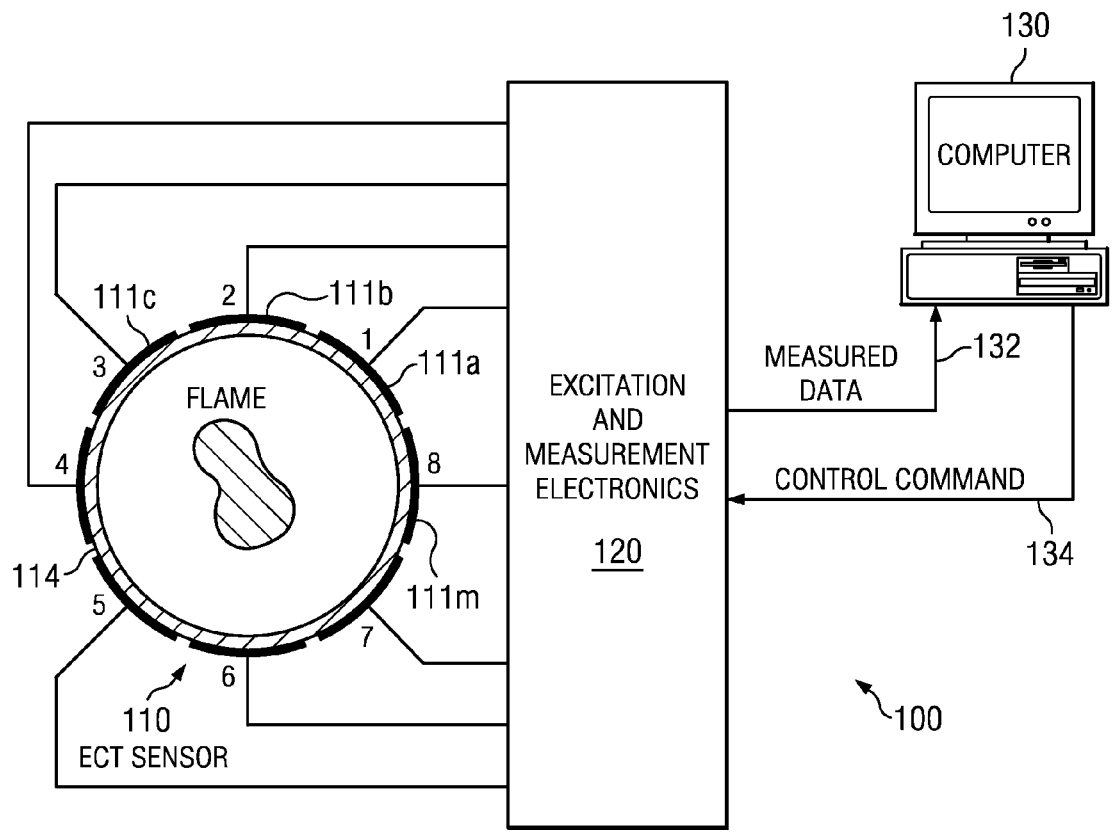
FIG. 1 is a schematic illustration of a conventional electronic capacitance tomography (ECT) system.
Figure 2:
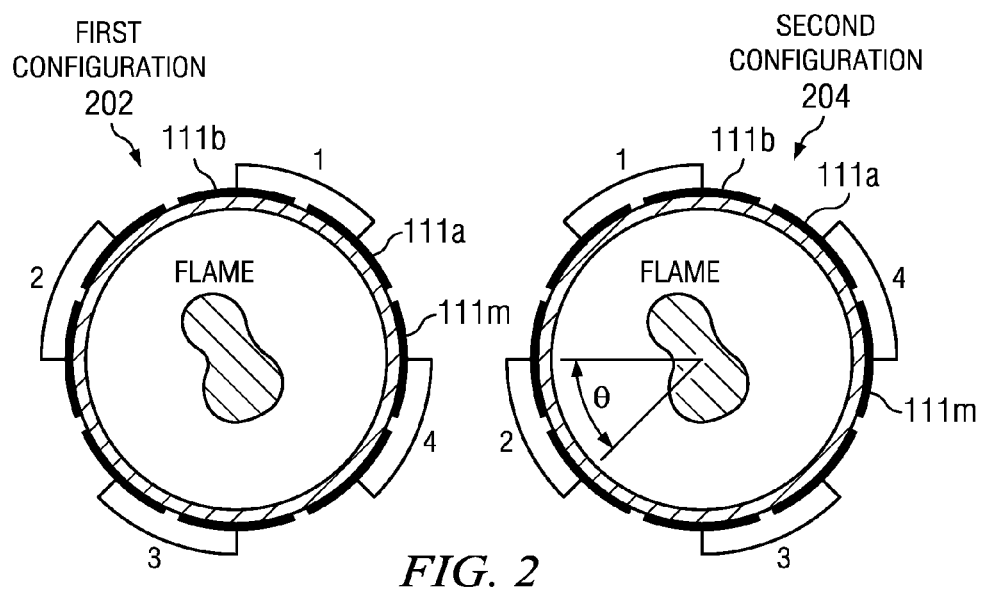
FIG. 2 is a schematic illustration of a conventional ECT system that uses grouping techniques to improve resolution without sacrificing signal-to-noise ratio.
Figure 3:
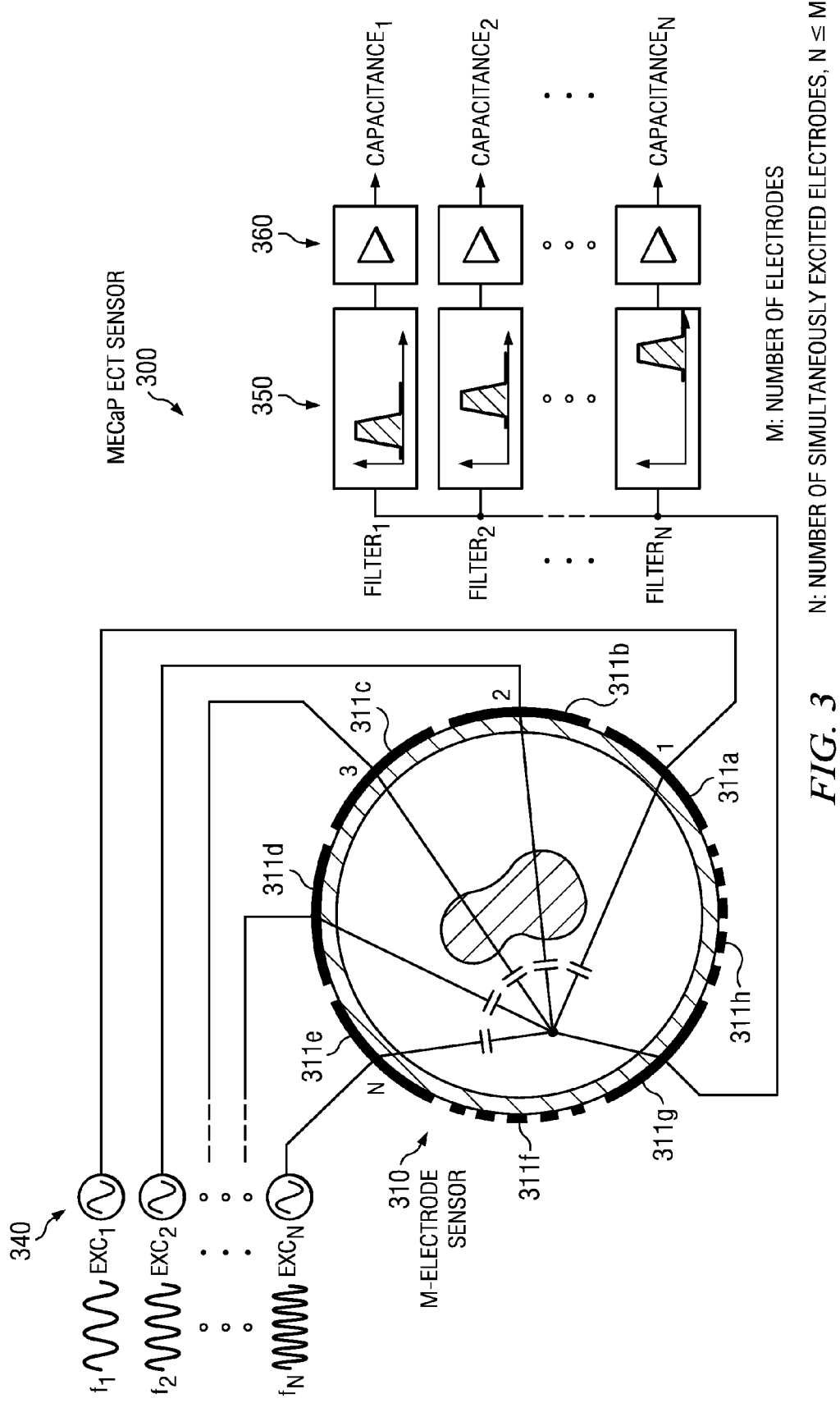
FIG. 3 is a schematic illustration of a multiple excitation capacitance polling (MECaP) ECT system according to embodiments of the present invention.

FIG. 3 shows an MECaP ECT system 300 capable of making multiple simultaneous inter-electrode capacitance measurements according to the present inventive techniques. As shown in FIG. 3, the system 300 includes a sensor 310 with eight electrodes 311a-311h (of course, other sensors may include any suitable number and configuration of electrodes). Oscillators 340 apply excitation signals to a subset of the electrodes 311a-311h; here, each oscillator 340 applies a respective signal to each of electrodes 311a-311e, where the respective signals are at different frequencies, i.e., $f_1, f_2, \ldots f_N$. Electrode 311g detects the signals from electrodes 311a-311e and couples them into bandpass filters 350, which transmit signals near their respective center frequencies, $f_1, f_2, \ldots f_N$, to amplifiers 360. The amplified, filtered signals can then be used to compute capacitances between the various pair-wise combinations of electrode 311g and each of electrodes 311a-311e.

For eight electrodes, as shown in FIG. 3, there are a total of M(M−1)/2=(8×7)/2=28 capacitance measurements would need to be performed within each scanning frame using the traditional AC techniques. In comparison, MECaP techniques involve only seven measurements as specified in Table 1. Because the delay caused by the additional bandpass filtering electronics will be on the order of nanoseconds, which is far less than the period of each measurement (typically 10 µs), the MECaP method enables a scanning speed increase of approximately three times relative to the traditional method. Other embodiments may enable even larger increases in scanning speed.

Table 1 shows that the excitation signals are applied to the electrodes in an increasing order instead of all at once. If all the excitation signals are applied at the same time, then the equations may become unsolvable. This progressive or successive excitation, which is more than just "parallel" vs. "serial" excitation, distinguishes MECaP from other ECT techniques.

TABLE 1

Measurement sequence for an eight-electrode sensor using the MECaP method.

| Measurement Sequence (n) | Simultaneously Measured Capacitance |
|---|---|
| 1 | $C_{12}$ |
| 2 | $C_{13}, C_{23}$ |
| 3 | $C_{14}, C_{24}, C_{34}$ |
| 4 | $C_{15}, C_{25}, C_{35}, C_{45}$ |
| 5 | $C_{16}, C_{26}, C_{36}, C_{46}, C_{56}$ |
| 6 | $C_{17}, C_{27}, C_{37}, C_{47}, C_{57}, C_{67}$ |
| 7 | $C_{18}, C_{28}, C_{38}, C_{48}, C_{58}, C_{68}, C_{78}$ |

Table 2 shows a comparison among traditional AC techniques, grouping techniques, and MECaP techniques with and without grouping. When grouping is not used, MECaP can reduce the total number of measurements to be performed in each scanning frame by $(M-1)(M-2)/2$. If the electrodes are grouped into K sections, MECaP techniques may reduce the number of measurements by $(M/K)(K-1)(K-2)/2$. For the traditional and grouping cases, the reduction in the number of measurements is proportional to the square of the parameter M or K. As a result, increasing the number of electrodes and/or sections in the sensor significantly increases the scanning speed.

TABLE 2

Numbers of Measurements for Different ECT Techniques

| ECT Techniques | No. of Meas. Per Frame | Reduction |
|---|---|---|
| Traditional method (no grouping) | $M(M-1)/2$ | |
| MECaP (no grouping) | $(M-1)$ | $(M-1)(M-2)/2$ |
| Traditional method (grouped into K sections) | $(M/K)K(K-1)/2$ | |
| MECaP (grouped into K sections) | $(M/K)(K-1)$ | $(M/K)(K-1)(K-2)/2$ |

Figure 4A:
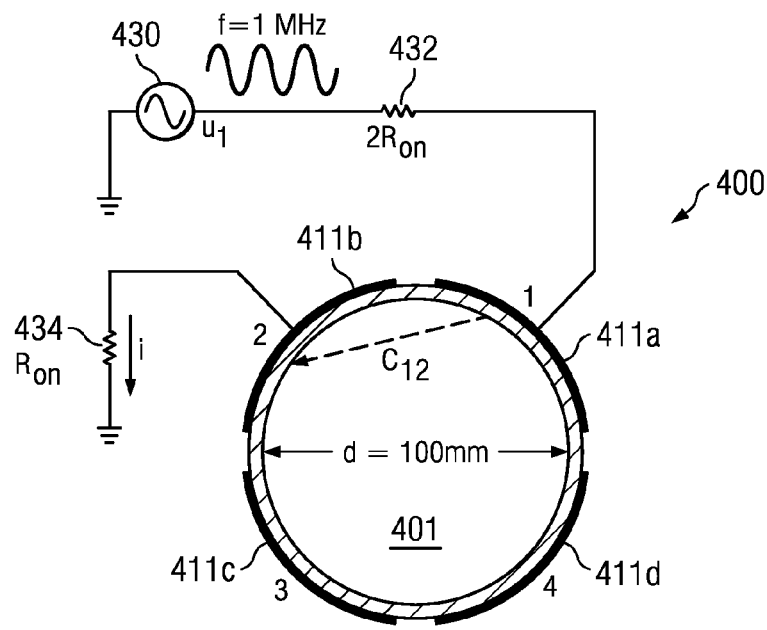
FIGS. 4A and 4B show schematic illustrations of a circuit model and a finite element model, respectively, for evaluating an MECaP ECT system.

FIG. 4A shows a circuit model 400 used to evaluate and simulate the electrode excitation process with MECaP techniques. In the example shown in FIG. 4A, a measurement object is modeled as a 100 mm diameter, 100 mm thick cylinder 401. Four electrodes 411a-411d are attached to the outer surface of the cylinder 401. A synthesizer 430, which is electrically coupled between ground and a first resistor 432, generates a sinusoidal excitation $u_1$ at a frequency of 1 MHz. Applying $u_1$ to the first electrode 411a and measuring the resulting current across a second resistor 434 coupled to the second electrode 411b makes it possible to measure the capacitance $C_{12}$ between the first and second electrodes 411a, 411b.

Figure 4B:
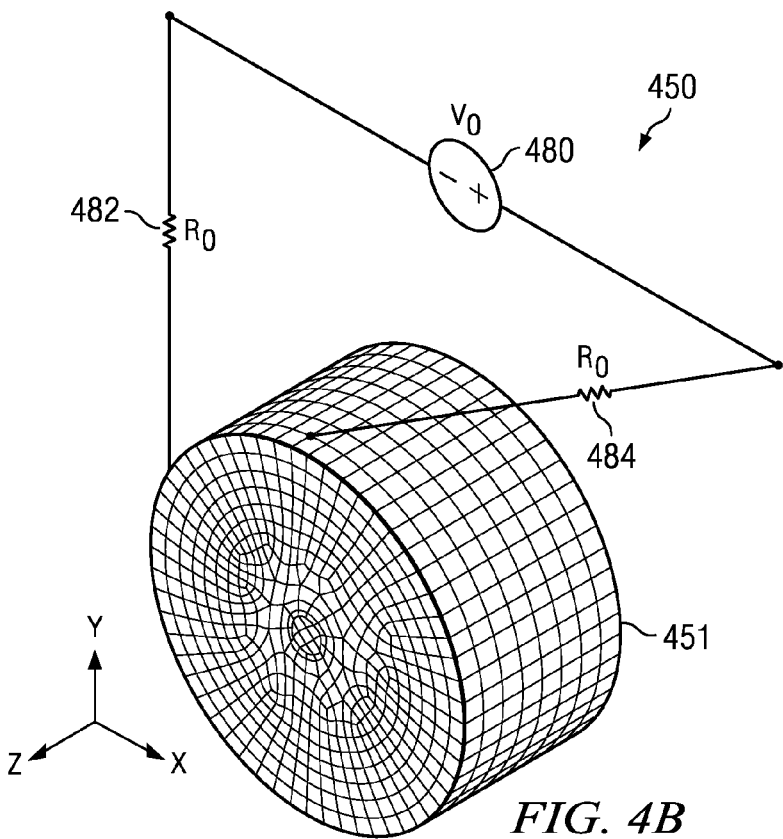

FIG. 4B shows a meshed finite-element model 450 used with the circuit model 400 of FIG. 4A to evaluate and simulate the electrode excitation process with MECaP techniques. Using finite-element analysis, the cylinder 401 of FIG. 4A is decomposed into numerous finite elements 451 arrayed on a cylindrical lattice. The capacitance between any given pair of elements 451 can be simulated by modeling a second electrical connection between the pair. In FIG. 4B, for example, the second electrical connection is shown as a first resistor 482 in series with a voltage source 480 and a second resistor 484. The behavior of the MECaP techniques can be simulated by evaluating the finite-element model 450 using standard numerical methods.

Figure 5:
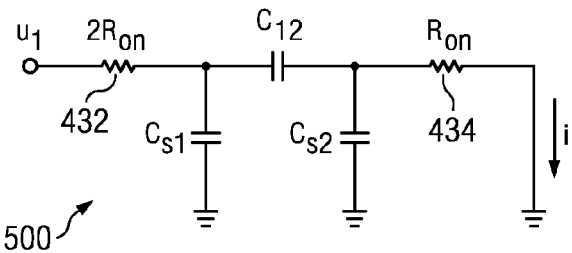
FIG. 5 shows a circuit diagram for an equivalent circuit for measuring $C_{12}$.

FIG. 5 shows an equivalent circuit 500 that can be used to measure $C_{12}$, the capacitance between electrodes 411a and 411b shown in FIG. 4B. The stray capacitance $C_{s1}$ and $C_{s2}$ are assumed to be zero for the purpose of simplification. In the simulation, the current, i, going through the second resistor 434 is measured and used with other parameters to calculate the capacitance values between pairs of electrodes.

For the purposes of non-limiting example, the CMOS switch resistance is taken to be $R_{on}$=35-60Ω; the excitation signal frequencies are $f_1$=1 MHz, $f_2$=2 MHz, ..., $f_n$=N MHz; and the excitation signal amplitude is taken to be 15 V. Further details for measuring the relevant capacitance values are presented below.

Measurement of $C_{12}$

During the first measurement, shown in FIG. 4, the first electrode 411a is excited by a sinusoidal wave $u_1$ with an amplitude of 15 V and a frequency of $f_1$=1 MHz. Based on the Kirchhoff's law, the following relationship can be established between the capacitance, $C_{12}$, the resistors, and the excitation signal:

$$u_1 = i \cdot \left( \frac{1}{j \cdot 2\pi f_1 C_{12}} + 3R_{on} \right) \quad (1)$$

Rearrangement yields:

$$C_{12} = \frac{1}{2\pi f_1 \sqrt{\frac{1}{a^2} - (3R_{on})^2}} \quad (2)$$

where $a=|A(i)/A(u_1)|$ is the ratio of the current amplitude to the voltage amplitude and $A(u_1)$=15 V.

Figure 6A:
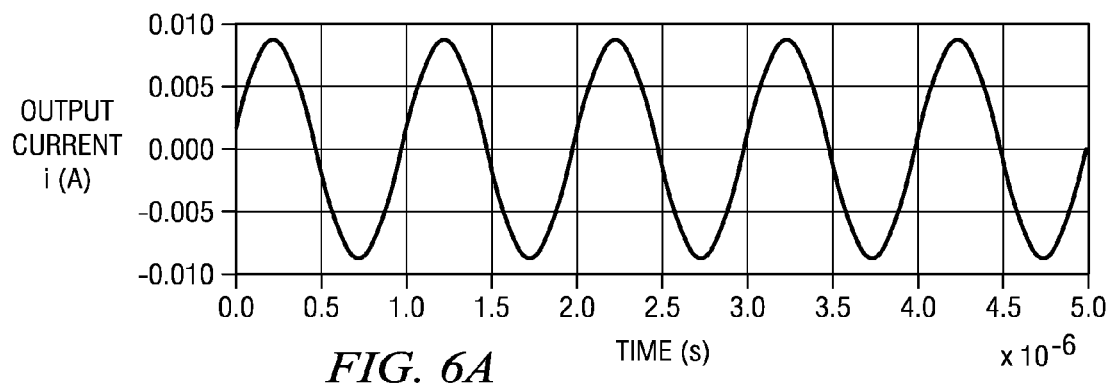
FIGS. 6A and 6B are plots of output current and signal magnitude, respectively, for measurement of $C_{12}$.
Figure 6B:
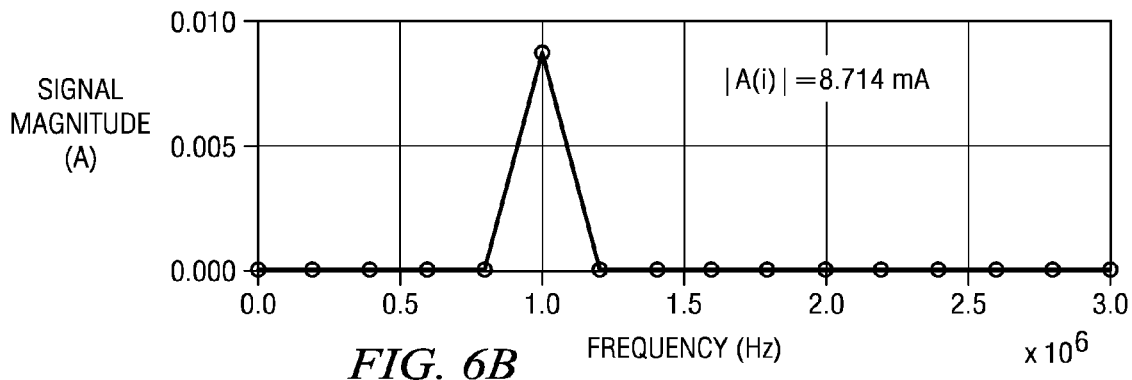

FIGS. 6A and 6B are plots of the output current and signal magnitude, respectively, going through the second resistor 434. As shown in FIG. 6B, the peak amplitude of the output current, A(i), is calculated as 8.714 mA. In practice, the peak value of the current can be measured by using a demodulator circuit. With the value of the second resistor 434 set to $R_{on}$=60Ω, the capacitance $C_{12}$ is 92 pF.

Measurement of $C_{13}$ and $C_{23}$

Figure 7A:
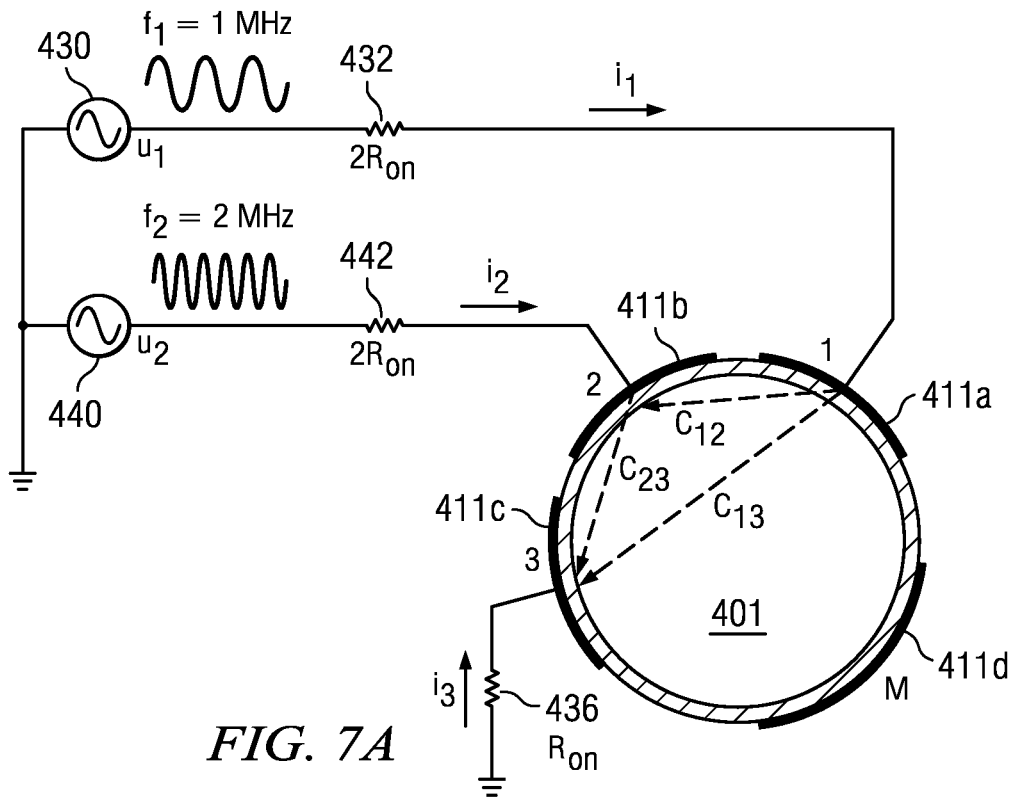
FIGS. 7A and 7B are a schematic diagram and a circuit diagram, respectively, of an MECaP evaluation model for measuring $C_{13}$ and $C_{23}$.

FIG. 7A is a schematic diagram of simultaneous measurement of capacitance between two different pairs of electrodes according to MECaP techniques. A first synthesizer 430 applies a first sinusoidal excitation signal $u_1$ at a frequency of $f_1$=1 MHz to the first electrode 411a. Simultaneously, a second synthesizer 440 applies a second sinusoidal excitation signal $u_2$ at a frequency of $f_2$=2 MHz to the second electrode 411b via a resistor 442. The third electrode 411c is used to collect the received signal.

Referring to the equivalent circuit shown in FIG. 5, the current going through the third electrode 411c can be measured by using the demodulator circuit referred to above. Thus, to determine the capacitance $C_{13}$ and $C_{23}$, relationships between the excitation signals, $u_1$ and $u_2$, and the output signal, $i_3$, need to be established.

Figure 7B:
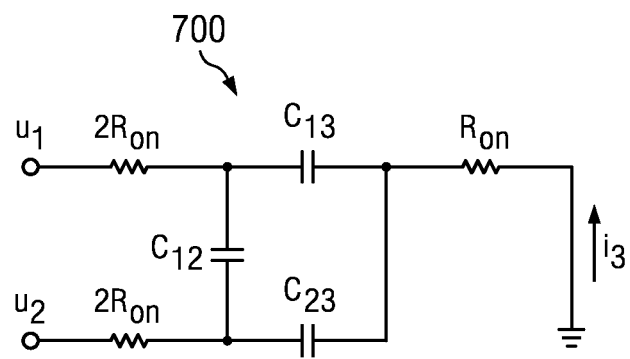

FIG. 7B is a diagram of a circuit 700 that can be used to establish a relationship among the excitation signals, $u_1$ and $u_2$, and the output signal, $i_3$. When multiple voltage sources are present in a linear circuit (as is the case in the system of FIG. 7A), each of them can be analyzed independently by assuming the others to be held at zero potential. Thus, to analyze the effect of the input voltage $u_i$ on the circuit, excitation signal 112 is first considered to be zero. Derivation yields the following relationship between the port currents, $i_1$ and $i_2$, and the input voltage, $u_1$:

$$\begin{cases} i_1 2R_{on} & -i_2(2R_{on}+Z_{12}) & & = u_1 \\ i_1 2R_{on} & + & +i_3(R_{on}+Z_{13}) & = u_1 \\ i_1 & +i_2 & -i_3 & = 0 \end{cases} \quad (3)$$

where $Z_{12}=1/(j\omega C_{12})$ and $Z_{13}=1/(j\omega C_{13})$. Since the capacitances to be measured are in the picofarad to femtofarad range, the corresponding impedance of these capacitances may be much larger than that of the CMOS switch resistance $R_{on}$. For instance, for a capacitance of 100 pF, the impedance at 1 MHz is calculated as $|Z_C|=1,592\Omega \gg R_{on}=60\Omega$. The impedance $|Z_C|$ may increase further if the capacitance decreases to the femtofarad level. Thus, the current flowing through the capacitances $C_{12}$ and $C_{23}$ is neglected in Eq. (3). This simplification is applied to the following analysis.

The relationship between the output current, $i_3$, and the first input voltage, $u_1$, can be expressed as:

$$\begin{aligned} a_{13} &= |H_{13}(j\omega)| \\ &= \left|\frac{i_3(j\omega)}{u_1(j\omega)}\right| \\ &= \left|\frac{1}{2R_{on}+(R_{on}+Z_{13})(4R_{on}+Z_{12})/(2R_{on}+Z_{12})}\right| \end{aligned} \quad (4)$$

Similarly, the relationship between the output current, $i_3$, and the second input voltage, $u_2$, can be expressed as:

$$\begin{aligned} a_{23} &= |H_{23}(j\omega)| \\ &= \left|\frac{i_3(j\omega)}{u_2(j\omega)}\right| \\ &= \left|\frac{1}{2R_{on}+(R_{on}+Z_{23})(4R_{on}+Z_{12})/(2R_{on}+Z_{12})}\right| \end{aligned} \quad (5)$$

Since the value of $C_{12}$ is known from the first measurement, the values for capacitances $C_{13}$ and $C_{23}$ can be found by substituting the values of $|H_{13}|$ and $|H_{23}|$ into Eqs. (4) and (5), respectively.

Figure 8A:
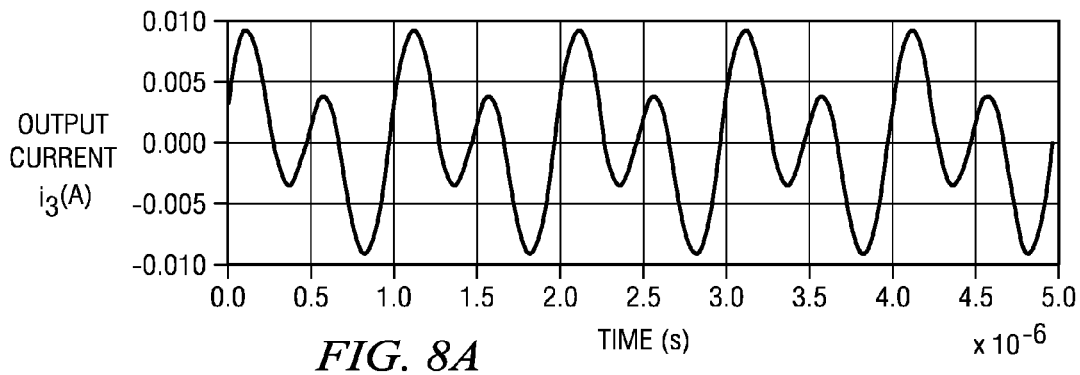
FIGS. 8A and 8B are plots of output current and signal magnitude, respectively, for measurement of $C_{13}$ and $C_{23}$.
Figure 8B:
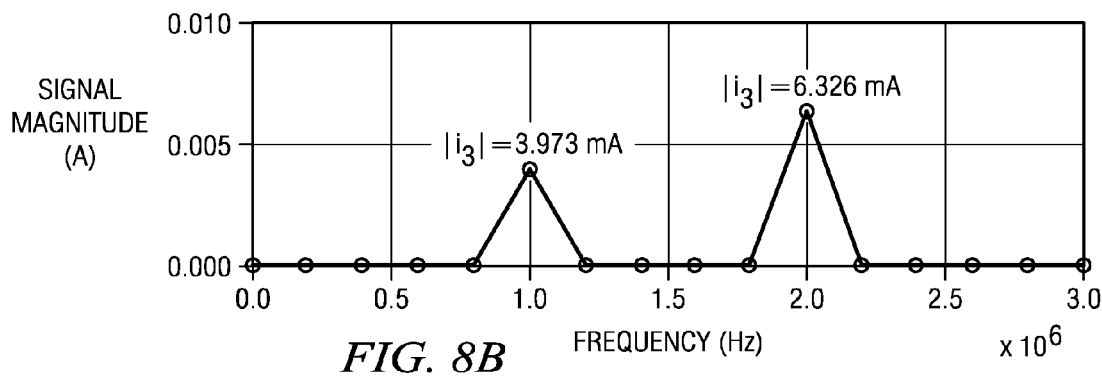

FIGS. 8A and 8B are plots of the output current and signal magnitude, respectively, going through the third resistor 436. The signal magnitude may be obtained by Fourier transforming the output current. As shown in FIG. 8B, there are two peaks in the output current: a first peak of 3.973 mA at 1 MHz corresponding to $C_{13}$ and a second peak of 6.326 mA at 2 MHz corresponding to $C_{23}$. These currents can be used to calculate the capacitance values as $C_{13}=92$ pF and $C_{23}=75$ pF. These are consistent with results obtained from measurement using a signal excitation.

Measurement of $C_{14}$, $C_{24}$, and $C_{34}$

The above described measurement may be continued by connecting electrodes 411a, 411b, and 411c to three excitation sources (not shown) simultaneously. The ratio of the output current to the input voltage, for each input signal, is then determined as above. Since the capacitance $C_{12}$, $C_{13}$, and $C_{23}$ are all known in the first two measurements, the capacitance between each of the excited electrodes 411a-411c and electrode 411d are the only unknown parameters in the above equations. They can be found by establishing the relationship between the three excitation voltages and the three filtered currents. For example, by considering that three AC voltages $u_1$, $u_2$, and $u_3$ are used to excite electrodes 411a, 411b, and 411c, respectively, the relationship between $u_1$ and the current going through electrode 411d can be established as:

$$\begin{cases} i_1 2R_{on} & -i_2(2R_{on}+Z_{12}) & & & = u_1 \\ i_1 2R_{on} & & -i_3(2R_{on}+Z_{13}) & & = u_1 \\ i_1 2R_{on} & & & +i_4(2R_{on}+Z_{14}) & = u_1 \\ i_1 & +i_2 & +i_3 & -i_4 & = 0 \end{cases} \quad (6)$$

where $Z_{14}=1/j\omega C_{14}$ is the impedance of $C_{14}$. The equations can be solved in a similar fashion as described with respect to Eqs. (4) and (5) to derive an expression for the capacitance $C_{14}$ as a function of the amplitude of $i_4$. Consequently, by measuring the amplitude of $i_4$ at the frequency of $u_1$, the capacitance $C_{14}$ can be determined. The same method can be applied to the determination of $C_{24}$ and $C_{34}$. As a result, a total of six capacitance values ($C_{12}$, $C_{13}$, $C_{23}$, $C_{14}$, $C_{24}$ and $C_{34}$) are determined in three measurement steps within a scanning frame.

Measurement of $C_{1N}$, $C_{2N}$, ..., $C_{(N-1)N}$

Figure 9:
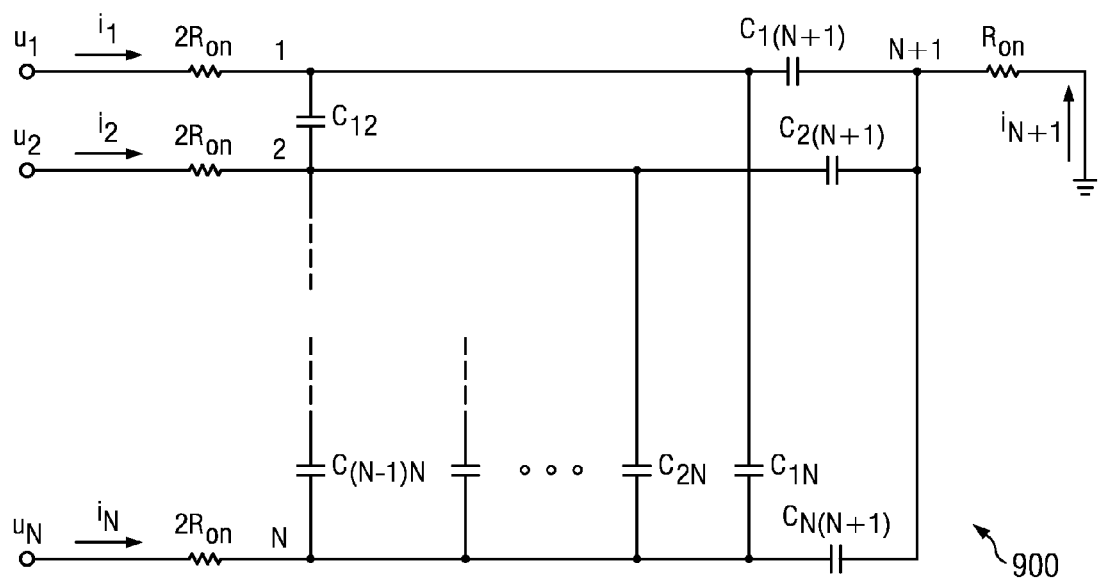
FIG. 9 is a circuit diagram for an equivalent circuit for measuring an arbitrary number of capacitances.

FIG. 9 shows a circuit model 900 that can be used to determine relationships between currents and capacitances for N simultaneously applied excitation signals. If (N−1)(N/2) capacitances have already been measured, then the capacitances, $C_{1N}$, $C_{2N}$, ..., $C_{(N-1)N}$, may be measured by applying N excitation signals $\{(u_1,f_1), (u_2,f_2), ..., (u_N, f_N)\}$ are applied to the electrodes 411a-411N. The last electrode, e.g., electrode 411(N+1), may be used as the receiving electrode. By assuming that $u_2=u_3=...u_{N-1}=0$, based on the Kirchhoff's law, the relationships between the excitation signal, $u_1$, and the port currents, $i_1, i_2, ..., i_N$, are given by the following N+1 equations:

$$\begin{cases} i_1 2R_{on} & -i_2(2R_{on}+Z_{12}) & & & = u_1 \\ i_1 2R_{on} & & -i_3(2R_{on}+Z_{13}) & & = u_1 \\ \vdots & & \cdots & & \vdots \\ i_1 2R_{on} & & & -i_{N+1}(2R_{on}+Z_{1(N+1)}) & = u_1 \\ i_1 & +i_2 & +i_3 & -i_{N+1} & = 0 \end{cases} \quad (7)$$

where $Z_{1k}=1/j\omega C_{1k}$, ($k=2, ..., N+1$) is the equivalent impedance between the first electrode (e.g., electrode 411a) and the N+1 electrode (e.g., electrode 411d).

Equation (7) can be rewritten in the matrix form:

$$\Psi_1 \cdot \vec{i} = \vec{u}_1 \quad (8)$$

where the matrices are given as follows:

$$\Psi_1 = \begin{bmatrix} 2R_{on} & -(2R_{on}+Z_{12}) & & & \\ 2R_{on} & & -(2R_{on}+Z_{13}) & & \\ \vdots & & & \cdots & \\ 2R_{on} & & & & -(2R_{on}+Z_{1(N+1)}) \\ 1 & 1 & 1 & & -1 \end{bmatrix},$$

-continued $$\vec{i} = \begin{bmatrix} i_1 \\ i_2 \\ \vdots \\ i_N \\ i_{N+1} \end{bmatrix}, \vec{u}_1 = \begin{bmatrix} u_1 \\ u_1 \\ \vdots \\ u_1 \\ 0 \end{bmatrix}$$

Based on Cramer's rule, the ratio between the current, $i_{N+1}$, and the excitation signal voltage, $u_1$, can be expressed as:

$$a_{1(N+1)} = \left| \frac{i_{N+1}}{u_1} \right| = \left| \frac{\det[\Theta_1]}{\det[\Psi_1]} \right| \tag{9}$$

where the det[ . . . ] is the matrix determinant and $\Theta_1$ is an (N+1)×(N+1) matrix formed by replacing the N+1 column of $\Psi_1$ by the column vector $\vec{u}_1/u_1$:

$$\Theta_1 = \begin{bmatrix} 2R_{on} & -(2R_{on}+Z_{12}) & & & & 1 \\ 2R_{on} & & -(2R_{on}+Z_{13}) & & & 1 \\ & & & \cdots & & 1 \\ 2R_{on} & & & & -(2R_{on}+Z_{1N}) & 1 \\ 2R_{on} & & & & & 1 \\ 1 & 1 & 1 & \cdots & 1 & 0 \end{bmatrix}$$

The term $\det[\Psi_1]$ is a first-order linear function of impedance $Z_{1(N+1)}=1/j\omega C_{1(N+1)}$. Thus, Eq. (9) can be expressed as:

$$\alpha C_{1(N+1)}^2 + \beta C_{1(N+1)} + \gamma = \frac{|\det[\Theta_1]|}{a_{1(N+1)}} \tag{10}$$

where $\alpha$, $\beta$, and $\gamma$ are real constants calculated from the term, $|\det[\Psi_1]|$. Given that the value of $a_{1(N+1)}$ can be measured experimentally, the capacitance $C_{1(N+1)}$ can be calculated by using the expression:

$$C_{1(N+1)} = \frac{\sqrt{\beta^2 + 4\alpha\left(\frac{|\det[\Theta_1]|}{a_{1(N+1)}} - \gamma\right)} - \beta}{2\alpha} \tag{11}$$

As a result, for any M-electrode cylinder, by measurement N, there are N(N+1)/2 capacitance values that can be calculated by measuring the magnitude of output signal at each excitation frequency. As a result, for an M-electrode ECT sensor, the total number of capacitance values, M·(M−1)/2, can be measured in M−1 measurements with MECaP techniques.

By using the measured capacitance values, $C_{ij}$, (i=1, . . . , N−1, j=2, . . . , N, i≠j), the two-dimensional distribution of material permittivity $\in(x, y)$ is given by:

$$\begin{cases} \nabla \cdot \varepsilon(x,y)\phi(x,y) = 0 \\ -\nabla \phi(x,y) = E \\ Q_{ij}/\Delta V = C_{ij} \end{cases} \tag{12}$$

where $\Phi(x, y)$ is the potential distribution; E is the electric field; $Q_{ij}$ is the charge across capacitance $C_{ij}$ and can be calculated by using the Gauss integral law; and $\Delta V$ is the voltage of the excitation signal. Applying Eq. (12) makes it possible to calculate the spatial distribution of materials within a volume using ECT.

Table 3 lists the maximum scanning speeds for different measurement techniques and numbers of electrodes. The maximum scanning speeds using MECaP and traditional AC techniques are calculated using optimal time per measurement values. Results from the two methods are compared in four different cases, where the number of the electrodes, M, is assumed to be 8, 12, 16, or 44 (grouped into 4 sections).

As shown in Table 3, when the number of simultaneously excited electrodes N approaches the upper limit $N_{max}=M-1$, the maximum scanning speed achieved with MECaP techniques can be increased from about two to eight times that of traditional AC techniques (without grouping). For example, for a twelve-electrode sensor, the total number of measurements performed per frame is 12×11/2=66. In comparison, a reduction to eleven measurements is possible using MECaP techniques when the number of simultaneously excited electrodes N is eleven. For grouped electrodes, MECaP techniques may achieve 2,000 frames per second, doubling the optimal speed reported elsewhere.

TABLE 3

Maximum Scanning Speed Achieved with Different ECT Techniques

|  |  | M (K) | | | |
| --- | --- | --- | --- | --- | --- |
|  |  | 8 (0) | 12 (0) | 16 (0) | 44 (4) |
|  | H | 28 | 66 | 120 | 66 |
| Traditional | # of Measurements/Frame | 28 | 66 | 120 | 66 |
| Method | Max Speed (Frame/sec) | 2,357[†] | 1,000[†] | 550[†] | 1,000[†] |
| MECaP | # of Measurements/Frame | 15 | 34 | 61 | 44 |
| $N_{max} = 2$ | Max Speed (Frame/sec) | 4,400 | 1,941 | 1,082 | 1500 |
|  | Increase % | 187% | 194% | 196% | 150% |
| MECaP | # of Measurements/Frame | 11 | 23 | 41 | 33 |
| $N_{max} = 3$ | Max Speed (Frame/sec) | 6,000 | 2,870 | 1,610 | 2,000 |
|  | Increase % | 254% | 286% | 293% | 200% |
| MECaP | # of Measurements/Frame | 9 | 18 | 32 |  |
| $N_{max} = 4$ | Max Speed (Frame/sec) | 7,333 | 3,667 | 2,063 |  |
|  | Increase % | 311% | 366% | 374% |  |

TABLE 3-continued

Maximum Scanning Speed Achieved with Different ECT Techniques

| | | M (K) | | | |
|---|---|---|---|---|---|
| | | 8 (0) | 12 (0) | 16 (0) | 44 (4) |
| MECaP $N_{max}=5$ | # of Measurements/Frame | 8 | 16 | 26 | |
| | Max Speed (Frame/sec) | 8,250 | 4,125 | 2,530 | |
| | Increase % | 350% | 413% | 460% | |
| MECaP $N_{max}=M-1$* | # of Measurements/Frame | 7 | 11 | 15 | 33 |
| | Max Speed (Frame/sec) | 9,429 | 6,000 | 4,400 | 2,000 |
| | Increase % | 400% | 600% | 800% | 200% |

Note:
*For grouped electrodes, $N_{max} = K - 1$
†The maximum scanning speeds for the traditional AC-method were calculated by referring to reported optimal time per measurement values.

In cases where $N_{max} < M-1$, when the number of activated electrodes reaches the upper limit, $N_{max}$, the remaining measurements continue with simultaneous excitation of $N_{max}$ electrodes until the end of the scanning frame. The expression of H in Table 2 is then modified as:

$$H = N_{max} + \left[\frac{M(M-1)/N_{max} - (N_{max}+1)}{2}\right]_{INT} \quad (13)$$

where $[X]_{INT}$ represents rounding the number X up to the nearest integer. When $N_{max}$ reaches the upper bound, $N_{max}=M-1$, the right-hand side of Eq. (13) reduces to M-1, which is consistent with the expression listed in Table 2. As an example, for $N_{max}=2$, the number of simultaneous excitations remains at two after completion of the second measurement, and the remaining capacitance values are measured using two simultaneous excitations. Therefore, for M=12, the total number of measurements per frame is H=2+(66-3)/2=34. The corresponding scanning speed is 1,941 frames/sec.

Figure 10:
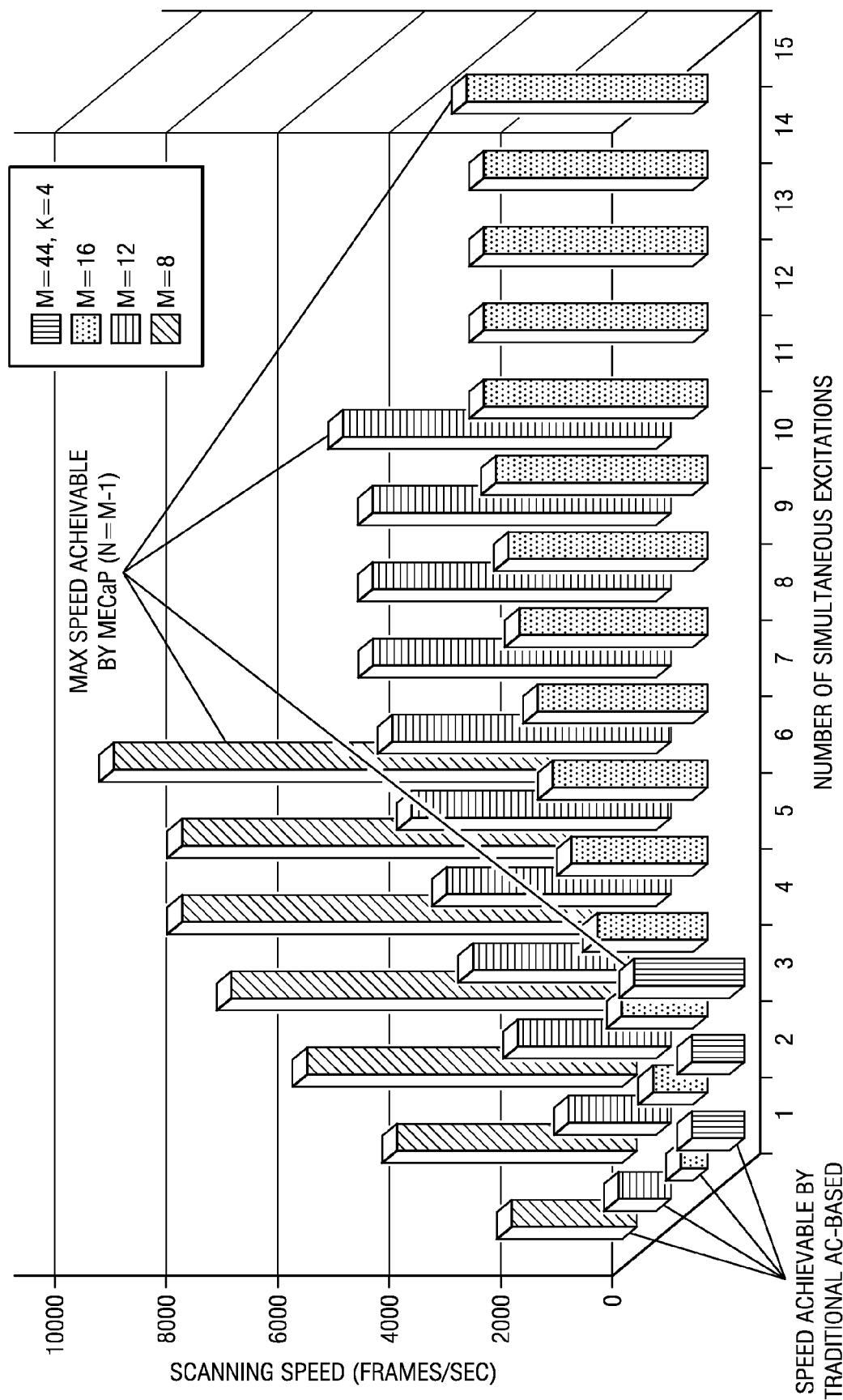
FIG. 10 is a bar graph showing scanning speed with MECaP techniques for different numbers of simultaneous excitations.

FIG. 10 is a plot of scanning speed versus the number of simultaneous excitations. The frequency bandwidth may limit the number of excitations that can be applied simultaneously to the electrodes. To illustrate the trend of scanning speed increase as a function of the number of simultaneous excitations, these two parameters are plotted in FIG. 10, for the four types of sensor configurations (M=8, 12, 16, and 44, with K=4). FIG. 10 shows that significant increase in capacitance scanning speed can be achieved for the same sensor configurations when MECaP techniques are applied compared to traditional AC techniques.

Computation Time for MECaP

Figure 11:
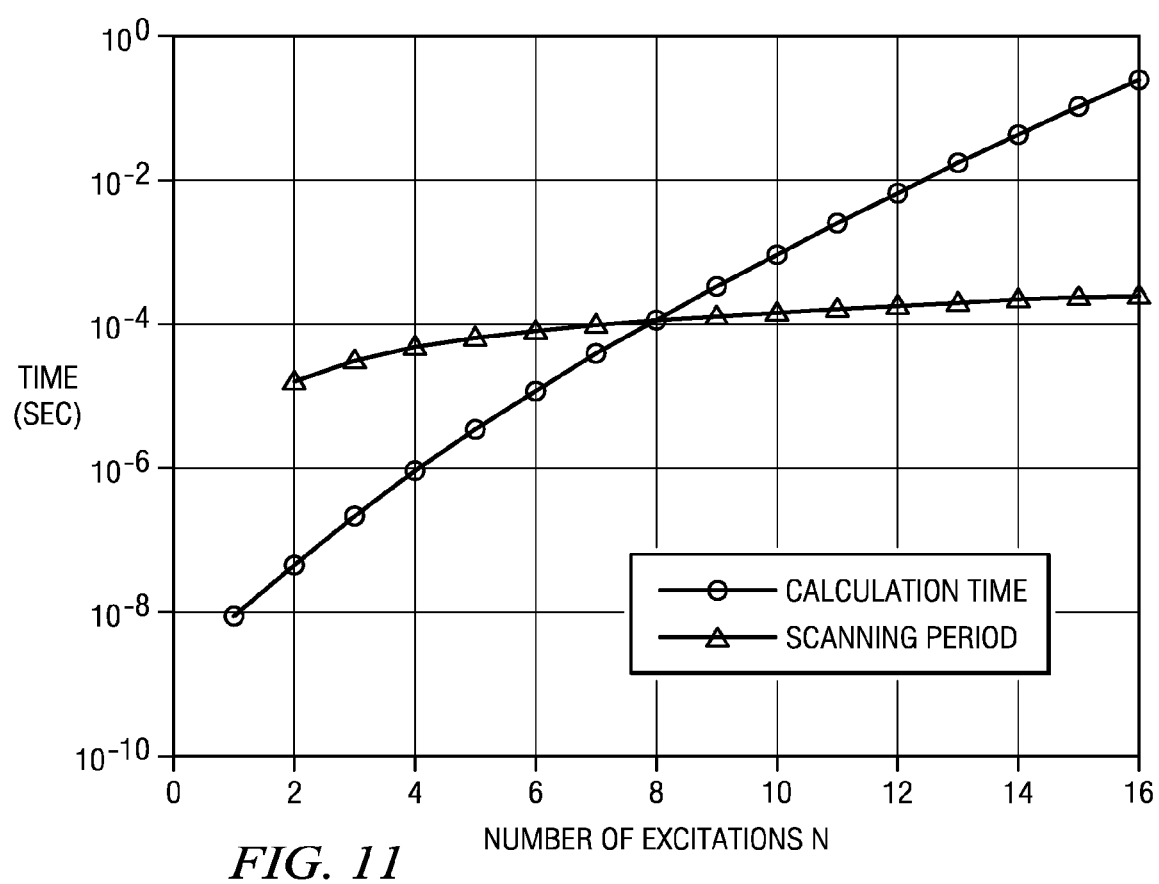
FIG. 11 is a plot of calculation time (circles) and scanning period (triangles) using MECaP techniques as a function of the number of simultaneous excitations.

FIG. 11 is a plot of estimated scanning period (triangles) and estimated calculation time (circles) using MECaP techniques for different numbers of excitations N. Compared with the traditional ECT techniques, extra calculation steps may be needed to perform the calculations described above, which, in turn, may affect the application of MECaP techniques to monitoring the object in real time.

The calculations below are based on the assumption that each complex number calculation (accumulation/multiplication) can be finished in one computer cycle and that each cycle takes 0.5 ns (i.e., the processor speed is 2 GHz or more). In cases where N electrodes are excited using AC signals, the calculation time may include three sub-calculations:

Calculation of matrix determinants in Eqs. (8) and (9). Both $\Theta_1$ and $\Psi_1$ are (N+1)×(N+1) matrices whose first columns include N+1 elements, whose $N^{th}$ columns include N elements, and whose other columns include two elements. Calculating each determinant requires one computer cycle per element, or $(N+1)N \cdot 2^{N-1}$ cycles, resulting a total number of cycles $CYC_{det}=(N+1)N \cdot 2^N$ Calculation of absolute values in Eq. (10). One accumulation and one multiplication are needed for $|det[\Theta_1]|$. For the term $|det[\Psi_1]|$, the value is tripled for the three terms $\alpha$, $\beta$, and $\gamma$, yielding five calculations total, or $CYC_{abs}=5$.

Calculation of second-order equation roots in Eq. (11). This may require nine computer cycles, or $CYC_{abs}=9$.

Since each excitation measurements measures N capacitors, the total number of cycles for each frame is:

$$CYC = \sum_{n=1}^{N} n[n(n+1)2^n + 5 + 8] \quad (13)$$

Referring again to FIG. 11, when N≤8, the calculation time is shorter than the scanning period, which allows for data processing in real time. This corresponds to an achievable scanning speed of 9,400 frames/sec.

Further embodiments of the present inventive MECaP technique may use different or optimal numbers of simultaneous excitations depending on trade-offs between the maximum scanning speed and the minimum differentiable frequency bandwidth. Embodiments may also use coding methods for sensing channel differentiation. For example, embodiments may use signal processing methods for channel coding that complement the frequency band allocation to ensure reliable channel separation and differentiation among multiple electrodes. Coding can enhance the immunity of the circuitry to noise interference and consequently, improve the robustness of the measurement circuitry.

In addition, different embodiments may employ different spatial distributions of electrodes. When used to sense capacitance of cylindrical bodies, such as engines, the electrodes may be distributed along the radial and axial directions to maximize the signal-to-noise ratio in sensing. Further embodiments may include embedded electronics for simultaneous electrode scanning. For instance, microcontroller-based parallel excitation and measurement circuitry with embedded firmware may control the switching of sensing channels and interfacing with a computer or other processor.

Embodiments of the invention can take the form of an entirely hardware embodiment, an entirely software embodiment, or an embodiment containing both hardware and software elements. In a preferred embodiment, the invention is implemented in software, which includes but is not limited to firmware, resident software, microcode, etc.

Furthermore, embodiments of the invention can take the form of a computer program product accessible from a computer-usable or non-transitory computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

While this invention has been particularly shown and described with references to example embodiments thereof, it will be understood by those skilled in the art that various changes in form and details may be made therein without departing from the scope of the invention encompassed by the appended claims. For example, the multiple excitation polling techniques disclosed herein may be applied to other forms of tomography, such as tomography performed with acoustic, optical, radio-frequency, or other suitable signals.

What is claimed is:

1. An apparatus for electronic capacitance tomography, the apparatus comprising:
   source and receiver electrodes capacitively coupled together in an arrangement to measure a spatial distribution of a substance within capacitive distance of at least one pair of source and receiver electrodes;
   an excitation module coupled to the source electrodes, the excitation module configured to excite sequentially a plurality of sets of source and receiver electrode pairs, wherein exciting a given set of the plurality of sets includes exciting simultaneously each source and receiver electrode pair of the given set with a different excitation signal, the different excitation signal being a voltage, the excitation module further configured to excite sequentially the plurality of the sets of source and receiver electrode pairs by exciting a set of source and receiver electrode pair and sequentially increasing a number of source electrodes for each subsequent sets of source and receiver electrode pairs of the plurality of sets of electrodes; and
   a measurement module coupled to the receiver electrodes, the measurement module configured to measure simultaneously capacitance between each source and receiver electrode pair by measuring a current, the measured capacitances representing the spatial distribution of the substance.

2. The apparatus of claim 1 wherein the different excitation signals are at different frequencies.

3. The apparatus of claim 1 wherein the different excitation signals are modulated with different codes.

4. The apparatus of claim 1 wherein each receiver electrode receives multiple excitation signals, and wherein each of the multiple excitation signals is applied simultaneously to more than one source electrode.

5. The apparatus of claim 4 wherein the measurement module is configured to simultaneously measure capacitances between each receiver electrode and every source electrode.

6. The apparatus of claim 1 further including:
   a discrimination module coupled to the measurement module, the discrimination module being configured to discriminate among signals received simultaneously at a given receiver electrode from more than one source electrode.

7. The apparatus of claim 6 wherein the discrimination module includes a filter bank configured to filter excitation signals at different frequencies.

8. The apparatus of claim 6 wherein the discrimination module performs a decomposition of signals detected by the receiver electrodes to measure the capacitances.

9. The apparatus of claim 1 further including:
   an imaging module coupled to the measurement module and configured to convert the measured capacitances to an indication of the spatial distribution of the substance.

10. The apparatus of claim 1 further including:
    a storage module coupled to the measurement module and configured to store the measured capacitances.

11. The apparatus of claim 10 further including:
    a postprocessing module coupled to the measurement module and configured to convert the stored, measured capacitances into indications of the spatial distribution of the substance.

12. The method of claim 1, wherein the excitation module is further configured to excite sequentially the plurality of sets of source and receiver electrode pairs by, for each sequential set of source and receiver electrode pairs, changing a receiver electrode.

13. A method of performing electronic capacitance tomography, the method comprising:
    exciting sequentially a plurality of sets of source and receiver electrode pairs, wherein exciting a given set of the plurality of sets includes exciting each source and receiver electrode pair of the given set simultaneously with a different excitation signal, the different excitation signal being a voltage, wherein exciting sequentially the plurality of sets of source and receiver electrode pairs includes exciting a set of one source and receiver electrode pair and sequentially increasing a number of source electrodes for each subsequent set of source and receiver electrode pairs of the plurality of sets of electrodes; and
    measuring capacitance between each source and receiver electrode pair by measuring a current.

14. The method of claim 13, further including:
generating the different excitation signals, each different excitation signals being at a different frequency.

15. The method of claim 13, further including:
modulating the different excitation signals with different codes.

16. The method of claim 13, wherein measuring capacitance includes measuring more than one excitation signal at a time.

17. The method of claim 13, further including:
discriminating among signals received simultaneously at the receiver electrode from the multiple source electrodes.

18. The method of claim 13 further including:
decomposing signals detected by the receiver electrodes to measure the capacitance.

19. The method of claim 13, further including:
processing the measured capacitance values to derive a spatial distribution of a substance disposed between the at least one receiver electrode and the multiple source electrodes.

20. The method of claim 19, further including:
storing the measured capacitance.

21. A non-transitory computer readable medium including code for performing electronic capacitance tomography, the code to be executed by a computer operable to:
excite sequentially a plurality of sets of source and receiver electrode pairs, wherein exciting a given set of the plurality of sets includes exciting each source and receiver electrode pair of the given set simultaneously with a different excitation signal, the different excitation signal being a voltage, wherein exciting sequentially the plurality of sets of source and receiver electrode pairs includes exciting of set of one source and receiver electrode pair and sequentially increasing a number of source electrodes for each subsequent set of source and receiver electrode pairs of the plurality of sets of electrodes; and
measure capacitance between each source and receiver electrode pair by measuring a current.

22. The computer readable medium of claim 21, wherein the code is further operable to:
generate the different excitation signals, each different excitation signals being at a different frequency.

23. The computer readable medium of claim 21, wherein the code is further operable to:
modulate the different excitation signals with different codes.

24. The computer readable medium of claim 21, wherein the code is further operable to:
measure more than one excitation signal at a time.

25. The computer readable medium of claim 21, wherein the code is further operable to:
discriminate among signals received simultaneously at the receiver electrode from the multiple source electrodes.

26. The computer readable medium of claim 21, wherein the code is further operable to:
decompose signals detected by the receiver electrodes to measure the capacitance.

27. The computer readable medium of claim 21, wherein the code is further operable to:
process the measured capacitance values to derive a spatial distribution of a9substance disposed between the at least one receiver electrode and the multiple source electrodes.

28. The computer readable medium of claim 21, wherein the code is further operable to:
store the measured capacitance.

29. An apparatus for performing electronic capacitance tomography, the apparatus comprising:
means for transmitting at least one excitation signal sequentially to a plurality of sets of source and receiver electrode pairs, wherein transmitting the at least one excitation signal to a given set of plurality of sets includes exciting simultaneously each source and receiver electrode pair of the given set, the at least on excitation signal being voltages, said means for transmitting further exciting a set of one source and receiver electrode pair, and sequentially increasing a number of source electrodes for each subsequent set of source and receiver electrode pairs of the plurality of sets of electrodes; and
means for measuring capacitance between each source and receiver electrode pair based on the at least one excitation signal by measuring a current.

* * * * *

UNITED STATES PATENT AND TRADEMARK OFFICE
CERTIFICATE OF CORRECTION

| | |
|---|---|
| PATENT NO. | : 8,762,084 B2 |
| APPLICATION NO. | : 12/826314 |
| DATED | : June 24, 2014 |
| INVENTOR(S) | : Robert X. Gao and Zhaoyan Fan |

Page 1 of 1

It is certified that error appears in the above-identified patent and that said Letters Patent is hereby corrected as shown below:

In the Claims

In Column 13, Claim 1, Line 66-67:
please delete "a set of source and receiver electrode pair"
and insert -- a set of one source and receiver electrode pair --

In Column 14, Claim 1, Line 1:
please delete "sets" and insert -- set --

In Column 15, Claim 21, Line 34:
please delete "includes exciting of set of one source"
and insert -- includes exciting a set of one source --

In Column 16, Claim 27, Line 19:
please delete "distribution of a9substance"
and insert -- distribution of a substance --

In Column 16, Claim 29, Line 32:
please delete "the at least on"
and insert -- the at least one --

Signed and Sealed this
Twenty-first Day of October, 2014

Michelle K. Lee
*Deputy Director of the United States Patent and Trademark Office*